United States Patent [19]

Asrar et al.

[11] Patent Number: 5,847,070
[45] Date of Patent: *Dec. 8, 1998

[54] HYDROXY ETHYL BIBENZOATE

[75] Inventors: Jawed Asrar, Chesterfield; David J. Weinkauff, Manchester; A. Hameed Bhombal, Chesterfield, all of Mo.

[73] Assignee: Monsanto Company, St. Louis, Mo.

[ * ] Notice: The terminal 10 months of this patent has been disclaimed.

[21] Appl. No.: 348,023

[22] Filed: Dec. 1, 1994

Related U.S. Application Data

[62] Division of Ser. No. 19,398, Feb. 18, 1993, Pat. No. 5,374,707.

[51] Int. Cl.$^6$ .................................................. C08G 63/02
[52] U.S. Cl. .................... 528/272; 524/431; 524/435; 524/462; 524/783; 524/784; 524/792; 525/437; 525/444; 528/275; 528/279; 528/283; 528/298; 528/300; 528/301; 528/302; 528/307; 528/304; 528/308.6; 560/8; 560/94; 560/190
[58] Field of Search .................................. 560/8, 94, 190; 528/272, 275, 279, 283, 298, 300, 301, 302, 307, 308, 308.6; 525/437, 444; 524/431, 435, 462, 783, 784, 792

[56] References Cited

U.S. PATENT DOCUMENTS

| | | | |
|---|---|---|---|
| Re. 30,783 | 10/1981 | Kleiner et al. ............................. | 528/287 |
| 3,641,112 | 2/1972 | Ichikawa et al. . | |
| 3,922,323 | 11/1975 | Reese et al. . | |
| 3,941,752 | 3/1976 | Kleiner et al. . | |
| 3,969,437 | 7/1976 | Shim . | |
| 4,014,858 | 3/1977 | Chipman et al. . | |
| 4,022,826 | 5/1977 | Lohmer et al. . | |
| 4,034,141 | 7/1977 | Duffy et al. ............................. | 428/473 |
| 4,096,202 | 6/1978 | Farnham et al. . | |
| 4,204,070 | 5/1980 | Suzuki et al. ............................. | 560/94 |
| 4,365,054 | 12/1982 | Astabley et al. ......................... | 528/277 |
| 4,440,924 | 4/1984 | Kuze et al. .............................. | 528/275 |
| 4,501,878 | 2/1985 | Adams .................................... | 528/286 |
| 4,656,241 | 4/1987 | Ilda et al. ................................ | 528/279 |
| 4,745,211 | 5/1988 | Jackson, Jr. et al. .................... | 560/80 |
| 4,959,450 | 9/1990 | Morris et al. ........................... | 528/272 |
| 4,970,286 | 11/1990 | Genz et al. .............................. | 528/193 |
| 4,983,707 | 1/1991 | Tanisake et al. ......................... | 528/193 |
| 4,983,777 | 1/1991 | Van Sickle .............................. | 568/568 |
| 4,985,501 | 1/1991 | Udipi ...................................... | 525/173 |
| 5,011,877 | 4/1991 | Morris et al. ............................ | 524/115 |
| 5,011,878 | 4/1991 | Morris et al. ............................ | 524/115 |
| 5,116,938 | 5/1992 | Engel-Badar et al. ................... | 528/272 |

FOREIGN PATENT DOCUMENTS

| | | |
|---|---|---|
| 0510591A2 | 10/1992 | European Pat. Off. . |
| 55-718 | 1/1980 | Japan . |
| 9302122 | 4/1993 | WIPO . |

*Primary Examiner*—John M. Cooney, Jr.
*Attorney, Agent, or Firm*—Fitzpatrick, Cella, Harper & Scinto

[57] ABSTRACT

New compounds including bis-β-hydroxy ethyl bibenzoate containing less than 2.5%, and preferably less than 1%, diethylene glycol and a process for the production of the bis-β-hydroxy ethyl bibenzoate by the condensation of 4,4'-biphenyl dicarboxylic acid and ethylene glycol at low temperature and pressure in the presence of a catalyst are disclosed. Use of the compounds to produce polyesters is also disclosed.

12 Claims, No Drawings

HYDROXY ETHYL BIBENZOATE

This application is a division of U.S. patent application Ser. No. 08/019,398 which was filed Feb. 18, 1993, now U.S. Pat. No. 5,374,707.

BACKGROUND OF THE INVENTION

This invention relates to a new hydroxy ethyl bibenzoate compound and a method of producing the compound. More particularly, this invention relates to a hydroxy ethyl bibenzoate compound containing less than 2.5% diethylene glycol. More particularly, this invention relates to a new bis-β-hydroxy ethyl bibenzoate containing less than 2.5% diethylene glycol, a method for making the compound and use of the compound in the production of polyesters.

DESCRIPTION OF THE PRIOR ART

Biphenyl dicarboxylic acid has been used as a monomer to produce polymers which may find use in high temperature applications. However, problems have been encountered in reducing undesired substituents attached to the bibenzoate. The methyl or ethyl ester is used instead of biphenyl dicarboxylic acid to overcome its poor reactivity as biphenyl dicarboxylic acid has a low solubility, a high melting point and melting is accompanied by dis-association. The synthesis of methyl or ethyl esters of biphenyl dicarboxylic acid is difficult, requiring high temperature and pressure. Although the methyl ester of biphenyl dicarboxylic acid can be produced from methanol and biphenyl dicarboxylic acid using a catalyst, a good, safe commercial process has not been developed. Use of the ester also adds process steps to produce and purify the ester. A large portion of the production of polyethylene terephthalate (PET) is based upon the use of terephthalic acid and ethylene glycol, not the dimethyl terephthalate, so the inclusion of another comonomer in the form of the methyl ester of a dicarboxylic acid is undesirable. The inclusion of the methyl or ethyl ester of a dicarboxylic acid results in the formation of methanol or ethanol which is distilled off with the ethylene glycol during the production of the PET. The ethylene glycol cannot be recycled in this process without being purified to remove the methanol or ethanol byproduct, adding cost and complexity to the process.

A need remains for a substantially pure, highly reactive material that can be used in processes based upon polyethylene terephthalate, dimethyl terephthalate and terephthalic acid to improve the properties of the materials.

SUMMARY OF THE INVENTION

It is an object of this invention to provide a substantially pure hydroxy ethyl bibenzoate.

It is another object of this invention to produce bis-β-hydroxy ethyl bibenzoate containing less than 2.5%, and preferably less than 1%, diethylene glycol.

It is a further object of this invention to provide a process for the production of bis-β-hydroxy ethyl bibenzoate containing less than 2.5%, and preferably less than 1%, diethylene glycol.

It is also an object of this invention to use the bis-β-hydroxy ethyl bibenzoate in the production of polyesters.

These and other objects are met by this invention which is directed to the production of bis-β-hydroxy ethyl bibenzoate containing less than 2.5%, and preferably less than 1%, diethylene glycol. The bis-β-hydroxy ethyl bibenzoate is produced by the condensation of 4,4'-biphenyl dicarboxylic acid and ethylene glycol at low temperature and pressure in the presence of a titanium based catalyst. The temperature of the process is preferably between about 180° C. and about 200° C., and is preferably about 197° C., and the process pressure is approximately atmospheric pressure. Bis-β-hydroxy ethyl bibenzoate is homopolymerized or copolymerized along with the condensation product of terephthalic acid and ethylene glycol in essentially the same manner as in the process for making polyethylene terephthalate.

DESCRIPTION OF THE PREFERRED EMBODIMENTS

The present invention relates to a substantially pure hydroxy ethyl bibenzoate compound. For this application the term "substantially pure" means a compound in which few of the repeating units contain undesirable substituents. Thus the substantially pure hydroxy ethyl bibenzoate of this invention includes less than 2.5% by weight diethylene glycol and preferably it includes less than 1% by weight diethylene glycol. A preferred compound is bis-β-hydroxy ethyl bibenzoate.

The preparation of hydroxy alkyl carboxylates such as, for example, bis-β-hydroxy ethyl bibenzoate produces diethylene glycol as a byproduct and some of the diethylene glycol reacts to become a substituent on the carboxylate compound. It is believed that this reaction is acid catalyzed. The inclusion of diethylene glycol as a substituent on the carboxylate compound is undesirable when the carboxylate is incorporated into other compositions as the diethylene glycol acts to decrease the glass transition temperature (Tg), an effect opposite that generally desired from the addition of the bibenzoate moiety.

Thus, the process of this invention which reduces the amount of diethylene glycol, and other similar substituents, included in the hydroxy ethyl bibenzoate produces a bibenzoate that can be incorporated in the production of other polymers or compositions without causing undesired effects. More specifically, the process of this invention produces a new compound, a bis hydroxy alkyl carboxylate and more specifically a bis-β-hydroxy ethyl bibenzoate containing less than 2.5% by weight diethylene glycol, and preferably containing less than 1% by weight diethylene glycol.

Two processes have been found effective for the production of the desired bis-β-hydroxy ethyl bibenzoate of this invention. In the broadest statement, the first process produces a bis hydroxy alkyl carboxylate containing less than 2.5% by weight oxyalkyl glycol by condensing a mixture of an aromatic dicarboxylic acid and a diol having a carbon chain with from 2 to 8 carbon atoms at a temperature between about 200° C. and about 260° C. and at a pressure between about 500 KPa and about 700 KPa. More specifically, in the first process, a mixture of biphenyl dicarboxylic acid and ethylene glycol is condensed at a temperature of between about 200° C. and about 260° C. and at a pressure between about 500 KPa and about 700 KPa. The ratio of ethylene glycol to biphenyl dicarboxylic acid in the mixture is at least 2.0 to 2.2 moles of ethylene glycol per mole of the biphenyl dicarboxylic acid and higher ratios may be used. The biphenyl dicarboxylic acid is preferably 4,4'-biphenyl dicarboxylic acid. The process temperature is preferably between about 200° C. and about 260° C. and more preferably is about 245° C. The process pressure is preferably between about 550 KPa and about 700 KPa. Use of this process produced bis-β-hydroxy ethyl bibenzoate having less than 2.5%, and often less than 1.5%, diethylene glycol by weight as an undesirable substituent.

The second process may be stated in its broadest sense as a process for the production of a bis hydroxy alkyl carboxylate containing less than 1% by weight of oxyalkyl glycol. A mixture of an aromatic dicarboxylic acid and a diol having a carbon chain with from 2 to 8 carbon atoms is condensed at a temperature between about 150° C. and about 250° C. and at atmospheric pressure in the presence of a catalyst selected from the group of catalysts based upon titanium, tin and iodine. More specifically, in the second process, a mixture of biphenyl dicarboxylic acid and ethylene glycol is condensed at a temperature of between about 150° C. and about 200° C. and at about atmospheric pressure in the presence of a titanium based catalyst. The biphenyl dicarboxylic acid is preferably 4,4'-biphenyl dicarboxylic acid. The biphenyl dicarboxylic acid and the ethylene glycol are mixed with at least two moles of ethylene glycol per mole of biphenyl dicarboxylic acid, and higher ratios such as, for example 4 to 1 or even 8 to 1 are preferred. The excess ethylene glycol is recycled during the process. The process temperature is preferably between about 180° C. and about 200° C., and more preferably is about 197° C., the boiling point of ethylene glycol. The process pressure is preferably about atmospheric. The catalyst is preferably a titanium based catalyst such as the Tyzor TE® catalyst produced by E. I. duPont de Nemours & Co., Inc. Use of this process produced bis-β-hydroxy ethyl bibenzoate having less than 1.0%, and often less than 0.1%, diethylene glycol by weight as an undesirable substituent.

The processes above have been described using the preferred 4,4'-biphenyl dicarboxylic acid. However, other diacids may also be used in the process to produce products similar to the bis-β-hydroxy ethyl bibenzoate which is produced when 4,4'-biphenyl dicarboxylic acid is the starting material. Other acceptable diacids are 3,4'-biphenyl dicarboxylic acid, terephthalic acid, diphenyl ether dicarboxylic acid, stilbene dicarboxylic acid, triphenyl dicarboxylic acid, naphthalene dicarboxylic acid and other aromatic dicarboxylic acids.

It is also possible to use diols other than ethylene glycol as the other starting reactant in this process. Propylene glycol, butylene glycol and other alkyl diols having a carbon chain with from 3 to about 8 carbon atoms may also be used to produce compounds similar to the bis-β-hydroxy ethyl bibenzoate. The use of butylene glycol, for example, will produce bis-hydroxy butyl bibenzoate. By using other diols, it is possible to produce two or more different bibenzoate compounds that can be used to produce copolymers such as, for example, a copolymer of bis-β-hydroxy ethyl bibenzoate and bis-hydroxy butyl bibenzoate.

A titanium based catalyst, Tyzor TE® produced by E. I. dupont de Nemours & Co., Inc., was used in the process described above. Other titanium based catalysts such as, for example, titanium isopropoxide, may also be used. While the titanium based catalyst is preferred, other catalysts such as, for example, tin based catalysts such as monobutyl dihydroxy tin and dibutyl tin oxide and catalysts such as tri-iodophenol may be used. The amount of catalyst used may be varied; however, as the amount of catalyst used was increased, the production of the undesired diethylene glycol was reduced. Excess catalyst may be washed from the reaction products and used again.

It is recognized that it may be necessary to change the process conditions set out above, particularly the temperature, when the alternate reactants are used.

Use of either process to produce bis-β-hydroxy ethyl bibenzoate has several advantages. The earlier use of the methyl or ethyl esters of biphenyl dicarboxylic acid requires extra process steps to make and purify the ester. These steps are eliminated by the use of the dicarboxylic acid to produce the bibenzoate. In addition, elimination of the use of the methyl and ethyl esters of biphenyl dicarboxylic acid in other processes such as the process to make polyethylene terephthalate eliminates an impurity from the ethylene glycol so that it can be recycled without purification steps to remove methanol or ethanol. This simplifies the process and improves the use of raw materials by allowing for the recycle of one of the reactants without other processing. The processes of this invention also produce bis-β-hydroxy ethyl bibenzoate having a smaller amount of diethylene glycol, and other undesirable impurities, than the material produced by the processes of the prior art so that the bibenzoate is more compatible with other compounds and may more easily be used in other manufacturing processes.

Incorporation of biphenyl dicarboxylate units into polyethylene terephthalate leads to improvement in certain properties of the polyethylene terephthalate such as, for example, tensile strength and modulus and heat and weather resistance. The incorporation of the biphenyl dicarboxylate moiety is usually achieved by condensing a mixture of terephthalic acid and the methyl or ethyl ester of biphenyl dicarboxylic acid with ethylene glycol. The methanol or ethanol that results, however, cause problems and, in addition, only a maximum of 5–10% of biphenyl dicarboxylic acid may be incorporated by this method. The melt polymerization process produces polyethylene terephthalate having an inherent viscosity of about 0.7 and it is necessary to use solid state polymerization in addition to melt polymerization to raise the inherent viscosity of the polyethylene terephthalate to the range of 1.1 to 1.2 that is needed for producing many products.

The addition of a few percent of biphenyl dicarboxylic acid in the form of the bis-β-hydoxy ethyl bibenzoate of this invention to the polyethylene terephthalate raises the glass transition temperature of the polyethylene terephthalate. In addition, it significantly improves the polymerization process for polyethylene terephthalate to produce polyethylene terephthalate having an inherent viscosity of approximately 1.1 to 1.2 without the previously required, and expensive, solid state polymerization steps. Bis-β-hydroxy ethyl bibenzoate is much more soluble than biphenyl dicarboxylic acid and it can, thus, be incorporated into the polyethylene terephthalate in much higher amounts. It is possible to produce a polymer of biphenyl dicarboxylic acid prepared using only bis-β-hydroxy ethyl bibenzoate having less than 2.5% by weight diethylene glycol. It is also possible to produce copolymers of biphenyl dicarboxylic acid and terephthalic acid wherein the copolymers have from 0.1% to 99.9%, by weight biphenyl dicarboxylic acid and from 99.9% to 0.1% by weight of terephthalic acid. Preferably the copolymers are prepared from 0.1% to 99.9% by weight bis-β-hydroxy ethyl bibenzoate and from 99.1% to 0.1% by weight terephthalic acid/ethylene glycol condensate, more preferably the copolymers are prepared from 5% to 95% by weight bis-β-hydroxy ethyl bibenzoate and from 95% to 5% by weight terephthalic acid/ethylene glycol condensate, and even more preferably the copolymers are prepared from 10% to 70% by weight bis-β-hydroxy ethyl bibenzoate and from 90% to 30% by weight terephthalic acid/ethylene glycol condensate. The bis-β-hydroxy ethyl bibenzoate preferably contains less than 2.5% by weight diethylene glycol and more preferably contains less than 1% by weight diethylene glycol.

The incorporation of bis-β-hydroxy ethyl bibenzoate into the production of polyethylene terephthalate offers significant benefits. It raises the glass transition temperature and the inherent viscosity of the polyethylene terephthalate and it allows the production of polymers having higher molecular weights. Moreover, the use of bis-β-hydroxy ethyl bibenzoate will allow the use of faster cycle times for the production of polyethylene terephthalate because bis-β-hydroxy ethyl bibenzoate has a much higher solubility than biphenyl dicarboxylic acid, or its methyl or ethyl esters. Thus, the use of bis-β-hydroxy ethyl bibenzoate offers improvement to the polymer end performance and to the process for the polyester production.

This invention will be explained in detail in accordance with the examples below, which are for illustrative purposes only and shall not limit the present invention.

EXAMPLES

In the examples below, from 2 to 8 moles of a diol, which was preferably ethylene glycol, and 1 mole of an aromatic dicarboxylic acid were mixed in a reactor under atmospheric pressure in the presence of varying types and amounts of catalyst. The mixture was heated to a temperature within the range of from about 150° C. to about 250° C. and maintained at that temperature for approximately 1 to 24 hours with water being removed. When the reaction was complete, the solution turned clear and it was then cooled to approximately 120° C. About 3 milliliters of a an alcohol such as, for example, methanol, ethanol or isopropanol, per theoretical gram of hydroxy alkyl bibenzoate were added to crystalize the hydroxy alkyl bibenzoate and to remove any remaining diol. The reaction mass was allowed to cool until the hydroxy alkyl bibenzoate crystallized. The hydroxy alkyl bibenzoate was filtered, washed and dried.

Example I

Ethylene glycol, 250 milliliters, was placed in a reactor that was equipped with a stirrer and a heating unit. A catalyst, as shown in Table 1, and 5 grams of 4,4'-biphenyl dicarboxylic acid (BDA) were added to the reactor. The reactor was maintained at atmospheric pressure as it was heated to reflux at about 195° C. while being stirred continuously. The reactor was maintained at that temperature for approximately 1 to 6 hours, depending upon the catalyst, with water being removed. When the reaction was complete, the solution turned clear and it was then allowed to cool to approximately ambient temperature. The product was analyzed to determine the presence of any diethylene glycol. The results are shown in Table 1.

Example II

The process of Example I was repeated with 5 grams of terephthalic acid (TA) as the diacid. The product was analyzed to determine the presence of any diethylene glycol. The results are shown in Table 1.

TABLE 1

| CATALYST | PROCESS TIME (HRS) | DIETHYLENE GLYCOL CONTENT | |
| --- | --- | --- | --- |
| | | IN BDA (WT %) | IN TA (WT %) |
| Dibutyl Tin Oxide | 2 | 0.1% | Not Detected |
| Titanium Chelate (Tyzor TE) | 1.5 | 0.02% | Not Detected |
| Tri-iodophenol | 5.5 | 3.91% | 4.9% |
| Titanium Isopropoxide | 1 | <0.01% | 0.06% |

Example III

A mixture of 31 grams of ethylene glycol and 61 grams of 4,4'-biphenyl dicarboxylic acid was placed in a reactor which was then sealed and purged with nitrogen four times. The reactor was initially pressurized to approximately 480 KPa with nitrogen and heat was added to raise the internal temperature of the reactor to approximately 240° C. After the temperature reached about 215° C., in approximately 25 minutes, the reactants were stirred constantly. When the reactor internal temperature reached the desired temperature of approximately 240° C., the pressure was reduced to about 480 KPa and held relatively constant for 90 minutes. Then the pressure was reduced to 350 KPa. The reaction was continued at these conditions for about 45 minutes at which time the pressure was reduced to atmospheric pressure and the esterification product was collected. No washing or other treatment was performed before the product was analyzed to determine the conversion and the presence of any diethylene glycol. The acid number was 29 mgKOH/g of sample which corresponds to a conversion of 92%. The amount of diethylene glycol present was measured as 1.87% by weight. If it is desired, the product could be washed with a solvent such as, for example, methanol to further reduce the amount of diethylene glycol present.

Example IV

The process of Example III was repeated with a mixture of 31 grams of ethylene glycol and 42 grams of terephthalic acid prepared in the reactor. The esterification product was collected and analyzed to determine the conversion and the presence of any diethylene glycol. The acid number was 53 mgKOH/g of sample which corresponds to a conversion of 88.2%. The amount of diethylene glycol present was measured as 2.15% by weight.

Example V

A mixture of 256.28 grams of ethylene glycol (4 moles) and 166.13 grams of terephthalic acid (1 mole) was charged to a reactor with 0.54 grams of Tyzor TE catalyst, approximately 135 parts per million (ppm) titanium based upon the weight of terephthalic acid charged. The reactor was heated slowly and the contents were stirred. When the reaction was nearly complete and the solution had turned mostly clear, after about 3.5 hours and at a temperature of approximately 200° C., an additional 166.13 grams of terephthalic acid (1 mole) were added to the reactor. Stirring and heating were continued until the reaction was again complete. The reaction mass was allowed to cool until the product crystallized. The product was analyzed to determine the presence of any diethylene glycol. The amount of diethylene glycol remaining in the product was about 0.60 weight percent.

Example VI

It is also possible to use more than one diacid in the reaction. A mixture of 248.3 grams of ethylene glycol (4 moles), 299.1 grams of terephthalic acid (1.8 mole) and 48.5 grams of 4,4'-biphenyl dicarboxylic acid (0.2 mole) were charged to a reactor with 0.65 grams of Tyzor TE catalyst. The reactor was heated slowly to initiate the reaction and the contents were stirred for about 8 hours until the reaction was complete. The reaction mass was allowed to cool until the product crystallized. The product was analyzed to determine the presence of any diethylene glycol. The amount of diethylene glycol remaining in the product was about 0.50 weight percent.

Example VII

The process of Example VI was repeated with a different catalyst. The reactants were the same, but 0.5 gram of dibutyl tin oxide was added in place of the Tyzor TE catalyst. The reaction took 12 hours to reach completion. The reaction mass was allowed to cool until the product crystallized. The product was analyzed to determine the presence of any diethylene glycol. The amount of diethylene glycol remaining in the product was about 0.89 weight percent.

Example VIII

The process of Example VI was repeated with a different catalyst. The reactants were the same, but 0.5 gram of antimony oxide was added in place of the Tyzor TE catalyst. The reaction took 24 hours to reach completion. The reaction mass was allowed to cool until the product crystallized. The product was analyzed to determine the presence of any diethylene glycol. The amount of diethylene glycol remaining in the product was about 3.74 weight percent.

Example IX

A mixture of 496.6 grams of ethylene glycol (8 moles) and 242.2 grams of 4,4'-biphenyl dicarboxylic acid (1 mole) were charged to a reactor with 0.21 grams of Tyzor TE catalyst. The reactor was heated slowly to initiate the reaction and the contents were stirred for about 25 hours until the reaction was complete. A sample of the unwashed product was allowed to cool and was then analyzed to determine the presence of any diethylene glycol. About 750 ml methanol were added to wash the reaction mass and the reflux was continued for about 30 minutes. The reaction mass was allowed to cool until the product crystallized. A sample of the washed product was analyzed to determine the presence of any diethylene glycol. The reaction time and the amount of diethylene glycol remaining in the unwashed and the washed product are shown in Table 2.

Example X

The process of Example IX was repeated with a greater amount of catalyst. The reactants were the same, but 1.22 grams of the Tyzor TE catalyst were added. The reaction took about 18.5 hours to reach completion. A sample of the washed product was analyzed to determine the presence of any diethylene glycol. The reaction time and the amount of diethylene glycol remaining in the washed product are shown in Table 2.

Example XI

The process of Example IX was repeated with a greater amount of catalyst. The reactants were the same, but 2.33 gram of the Tyzor TE catalyst were added. The reaction took about 12 hours to reach completion. A sample of the unwashed and of the washed product was analyzed to determine the presence of any diethylene glycol. The reaction time and the amount of diethylene glycol remaining in the unwashed and the washed product are shown in Table 2.

TABLE 2

| EXRMPLE | CATALYST AMOUNT | REACTION TIME | DIETHYLENE GLYCOL CONTENT | |
|---|---|---|---|---|
| | | | UNWASHED SAMPLE (Wt %) | WASHED SAMPLE (Wt %) |
| IX | 0.21 grams | 25 Hrs. | 1.79 wt % | 0.85 wt % |
| X | 1.22 grams | 18.5 Hrs. | unknown | 0.24 wt % |
| XI | 2.33 grams | 12 Hrs. | 0.63 wt % | 0.15 wt % |

Example XII

A round bottom flask was filled with 18 grams of the esterification product of ethylene glycol and terephthalic acid, where the molar ratio was 1.2 to 1 respectively and the diethylene glycol content was 1.32% by weight, 2 grams of the esterification product of ethylene glycol and 4,4'-biphenyl dicarboxylic acid (the bis-β-hydroxy ethyl bibenzoate of this invention), where the molar ratio was 2 to 1 respectively and the diethylene glycol content was 2.38% by weight, and 0.02 grams of antimony oxide, $Sb_2O_3$. The flask was fitted to a vacuum system, filled with nitrogen, and evacuated three times to remove all oxygen. The flask was then placed in a salt bath preheated to 250° C. The temperature was raised from 250° C. to 285° C. over a period of 1 hour and ethylene glycol was distilled off. After 90 minutes at 285° C., the pressure was reduced to 1.42 mmHg in 15 minutes. The pressure was further reduced over a period of 45 minutes to 0.20 mmHg. The reaction was continued at these conditions for an additional 30 minutes to complete the polymerization and the heat and vacuum were removed. The resulting polymer had an inherent viscosity of 1.08 at a concentration of 0.5 grams/deciliter in a solution of 60% phenol/40% tetrachloroethane at 25° C. The polymer had a diethylene glycol content of 1.72% by weight, and the glass transition temperature and the melting point determined by differential scanning calorimeter were 83° C. and 229° C. respectively.

Example XIII

The process of Example XII was repeated. Polymerization was conducted in the same manner as described in Example XII except the esterification product of ethylene glycol and terephthalic acid contained 3.96% by weight diethylene glycol and the bis-β-hydroxy ethyl bibenzoate also contained 3.96% by weight diethylene glycol. The polymer produced using these starting materials had an inherent viscosity of 1.09. The polymer had a diethylene glycol content of 4.07% by weight, and the glass transition temperature and the melting point were 78° C. and 217° C. respectively.

Example XIV

The process of Example XII was repeated. Polymerization was conducted in the same manner as described in Example XII except 19 grams of the esterification product of ethylene glycol and terephthalic acid containing 1.00% by weight diethylene glycol and 1 gram of the bis-β-hydroxy ethyl bibenzoate containing 0.15% by weight diethylene glycol were used. The polymer produced using these starting materials had an inherent viscosity of 1.12. The glass transition temperature was 81° C.

Example XV

A round bottom flask was filled with 6 grams of the esterification product of ethylene glycol and terephthalic acid, where the molar ratio was 1.2 to 1 respectively and the diethylene glycol content was 1.00% by weight, 14 grams of the esterification product of ethylene glycol and 4,4'-biphenyl dicarboxylic acid (the bis-β-hydroxy ethyl bibenzoate of this invention), where the molar ratio was 2 to 1 respectively and the diethylene glycol content was 0.15% by weight, and 0.004 grams of antimony oxide, $Sb_2O_3$. The flask was fitted to a vacuum system, filled with nitrogen, and evacuated three times to remove all oxygen. The flask was then placed in a salt bath preheated to 250° C. The temperature was raised from 250° C. to 285° C. over a period of 1 hour and ethylene glycol was distilled off. After 90 minutes at 285° C., the pressure was reduced to 1.42 mmHg in 15 minutes. The pressure was further reduced over a period of 45 minutes to 0.20 mmHg. The reaction was continued at these conditions for an additional 30 minutes to complete the polymerization and the heat and vacuum were removed. The resulting polymer had an inherent viscosity of 1.28 at a concentration of 0.5 grams/deciliter in a solution of 60% phenol/40% tetrachloroethane at 25° C. The glass transition temperature and the melting point determined by the differential scanning calorimeter were 111° C. and 278° C. respectively.

Example XVI

A round bottom flask was filled with 12 grams of the esterification product of ethylene glycol and terephthalic acid, where the molar ratio was 1.2 to 1 respectively and the diethylene glycol content was 1.00% by weight, 8 grams of the esterification product of ethylene glycol and 4,4'-biphenyl dicarboxylic acid (bis-β-hydroxy ethyl bibenzoate), where the molar ratio was 2 to 1 respectively and the diethylene glycol content was 0.15% by weight, and 0.004 grams of antimony oxide, $Sb_2O_3$. The flask was fitted to a vacuum system, filled with nitrogen, and evacuated three times to remove all oxygen. The flask was then placed in a salt bath preheated to 250° C. The temperature was raised from 250° C. to 285° C. over a period of 1 hour and ethylene glycol was distilled off. After 90 minutes at 285° C., the pressure was reduced to 1.42 mmHg in 15 minutes. The pressure was further reduced over a period of 45 minutes to 0.20 mmHg. The reaction was continued at these conditions for an additional 30 minutes to complete the polymerization and the heat and vacuum were removed. The resulting polymer had an inherent viscosity of 1.1 at a concentration of 0.5 grams/deciliter in a solution of 60% phenol/40% tetrachloroethane at 25° C. The glass transition temperature determined by differential scanning calorimeter was 96° C. There was no melting endotherm observed in the differential scanning calorimeter.

Example XVII

A round bottom flask was filled with 20 grams of the esterification product of ethylene glycol and 4,4'-biphenyl dicarboxylic acid (bis-β-hydroxy ethyl bibenzoate), where the molar ratio was 2 to 1 respectively and the diethylene glycol content was 0.15% by weight, and 0.004 grams of antimony oxide, $Sb_2O_3$. The flask was fitted to a vacuum system, filled with nitrogen, and evacuated three times to remove all oxygen. The flask was then placed in a salt bath preheated to 250° C. The temperature was raised from 250° C. to.292° C. over a period of 15 minutes and ethylene glycol was distilled off. Within 30 minutes the temperature was raised to 350° C. and the pressure was reduced to 0.5 mmHg. The reaction was continued at these conditions for an additional 15 minutes to complete the polymerization and the heat and vacuum were removed. No glass transition temperature was observed in the differential scanning calorimeter. The melting point determined by differential scanning calorimeter was 340° C. and 229° C. respectively.

Example XVIII

A reactor that was equipped with a stirrer and a heating unit was filled with 120 grams of 1,4-butanediol, 50 grams of 4,4'-biphenyl dicarboxylic acid and 0.12 grams of dihydroxy butyl tin hydrochloride. The reactor was maintained at atmospheric pressure as it was heated to reflux at about 200° C. while being stirred continuously. The reactor was maintained at that temperature for approximately 40 minutes, with water being removed, when a thin slurry was formed. About 10 minutes later, the solution turned clear and it was then allowed to cool to approximately ambient temperature. The product was bis hydroxy butyl bibenzoate.

Example XIX

A round bottom flask was filled with 8 grams of the esterification product of 1,4-butanediol and 4,4'-biphenyl dicarboxylic acid (bis hydroxy butyl bibenzoate), where the molar ratio was 2 to 1 respectively, 12 grams of the esterification product of ethylene glycol and 4,4'-biphenyl dicarboxylic acid (bis-β-hydroxy ethyl bibenzoate), where the molar ratio was 2 to 1 respectively and the diethylene glycol content was 0.15% by weight, and 0.018 grams of antimony oxide, $Sb_2O_3$. The flask was fitted to a vacuum system, filled with nitrogen, and evacuated three times to remove all oxygen. The flask was then placed in a salt bath preheated to 250° C. The temperature was raised from 250° C. to 285° C. over a period of 1 hour and ethylene glycol was distilled off. After 90 minutes at 285° C., the pressure was reduced to 1.24 mmHg in 10 minutes. The pressure was further reduced over a period of 30 minutes to 0.30 mmHg. The temperature was then raised to 290° C. and the pressure was reduced to 0.20 mmHg. The reaction was continued at these conditions for an additional 45 minutes to complete the polymerization and the heat and vacuum were then removed. The polymer had an ethylene glycol content of 44% and a butanediol derived content of 66%. The melting points determined by differential scanning calorimeter were 212° C. and 265° C.

We claim:

1. A process for the production of a bis hydroxy alkyl carboxylate containing less than 1% by weight oxyalkyl glycol comprising condensing a mixture of an aromatic dicarboxylic acid selected from the group consisting of 4,4'-biphenyl dicarboxylic acid, 3,4'-biphenyl dicarboxylic acid, diphenyl ether dicarboxylic acid, stilbene dicarboxylic acid, and triphenyl dicarboxylic acid and a diol having a carbon chain having from 2 to 8 carbon atoms at a temperature between about 150° C. and about 200° C. and at atmospheric pressure in the presence of a catalyst selected from the group of catalysts based upon titanium, tin and iodine.

2. The process of claim 1 wherein the aromatic dicarboxylic acid is 4,4'-biphenyl dicarboxylic acid.

3. The process of claim 1 wherein the diol has a carbon chain having from 2 to 4 carbon atoms.

4. The process of claim 3 wherein the diol is ethylene glycol, propylene glycol or butylene glycol.

5. The process of claim 4 wherein the diol is ethylene glycol.

6. The process of claim 1 wherein the catalyst is a titanium based catalyst.

7. The process of claim 1 wherein the catalyst is a tin based catalyst.

8. A process for the production of bis-β-hydroxy ethyl bibenzoate containing less than 1% by weight diethylene glycol comprising condensing a mixture of 4,4'-biphenyl dicarboxylic acid and ethylene glycol at a temperature between 150° C. and 197° C. and at about atmospheric pressure in the presence of a catalyst selected from the group consisting of catalysts based upon titanium, tin and iodine.

9. The process of claim 8 wherein the catalyst is a titanium based catalyst.

10. A process for the production of bis hydroxy butyl bibenzoate comprising condensing a mixture of 4,4'-biphenyl dicarboxylic acid and butylene glycol at a temperature between 150° C. and 250° C. and at about atmospheric pressure in the presence of a catalyst selected from the group consisting of catalysts based upon titanium, tin and iodine.

11. The process of claim 10 wherein the catalyst is a titanium based catalyst.

12. The process of claim 10 wherein the catalyst is a tin based catalyst.

* * * * *